(12) United States Patent
Masi

(10) Patent No.: US 11,857,682 B2
(45) Date of Patent: Jan. 2, 2024

(54) HYALURONATE COMPOSITIONS AND SOFT TISSUE FILLERS

(71) Applicant: AMC Group LLC, Del Mar, CA (US)

(72) Inventor: Louis Masi, Del Mar, CA (US)

(73) Assignee: AMC Group LLC, Del Mar, CA (US)

( * ) Notice: Subject to any disclaimer, the term of this patent is extended or adjusted under 35 U.S.C. 154(b) by 281 days.

(21) Appl. No.: 17/229,200

(22) Filed: Apr. 13, 2021

(65) Prior Publication Data

US 2021/0308055 A1 Oct. 7, 2021

Related U.S. Application Data

(62) Division of application No. 16/841,861, filed on Apr. 7, 2020, now Pat. No. 11,058,640.

(51) Int. Cl.
*A61K 9/16* (2006.01)
*A61K 8/73* (2006.01)
(Continued)

(52) U.S. Cl.
CPC ............ *A61K 9/1652* (2013.01); *A61K 8/735* (2013.01); *A61K 9/0019* (2013.01); *A61K 9/06* (2013.01);
(Continued)

(58) Field of Classification Search
None
See application file for complete search history.

(56) References Cited

U.S. PATENT DOCUMENTS 8,287,594 B2 10/2012 Cragg et al.
8,450,475 B2 5/2013 Lebreton
(Continued)

FOREIGN PATENT DOCUMENTS

KR 2018067197 A 7/2018
WO 2011086458 A1 7/2011
WO 2012167079 A2 12/2012

OTHER PUBLICATIONS

International Search Report and Written Opinion for International Application PCT/US2021/025882; International Filing Date: Apr. 6, 2021; dated Jun. 30, 2021; 8 pages.
(Continued)

*Primary Examiner* — Bethany P Barham
*Assistant Examiner* — Barbara S Frazier
(74) *Attorney, Agent, or Firm* — Karen A. LeCuyer; DeWitt LLP

(57) ABSTRACT

A method of making a modified hyaluronate composition including providing an aqueous solution of uncrosslinked hyaluronic acid or sodium hyaluronate in unbuffered 135 to 200 mM NaCl, crosslinking the uncrosslinked hyaluronic acid or sodium hyaluronate in the aqueous solution with a dialdehyde or disulfide crosslinking agent to provide crude modified hyaluronate having a soluble fraction and a crosslinked fraction with a 10% to 98% degree of crosslinking, centrifuging the crude modified hyaluronate and removing at least a portion of the soluble fraction, and optionally repeating the centrifuging and removing until the modified hyaluronate has less than 10% by weight of the soluble fraction based on the total weight of hyaluronate, with a soluble fraction polydispersity (Mw/Mn) of 1 to 1.6, an Rh of the crosslinked fraction of 150 nm to 2000 nm, and an Rz of the crosslinked fraction of 50 nm to 700 nm, wherein Rh>Rz.

13 Claims, 4 Drawing Sheets

(51) Int. Cl.
  A61K 9/00    (2006.01)
  A61K 9/06    (2006.01)
  A61K 31/167  (2006.01)
  A61K 47/42   (2017.01)
  A61Q 19/08   (2006.01)

(52) U.S. Cl.
  CPC .......... *A61K 9/1658* (2013.01); *A61K 31/167* (2013.01); *A61K 47/42* (2013.01); *A61Q 19/08* (2013.01)

(56) References Cited

U.S. PATENT DOCUMENTS

| | | | |
|---|---|---|---|
| 9,393,263 | B2 | 7/2016 | Liu et al. |
| 9,789,222 | B2 | 10/2017 | Masi |
| 10,391,202 | B2 | 8/2019 | Lebreton |
| 10,485,896 | B2 | 11/2019 | Lebreton |
| 2002/0049281 | A1 | 4/2002 | Zhao et al. |
| 2015/0366976 | A1 | 12/2015 | Nguyen et al. |
| 2018/0177707 | A1 | 6/2018 | Belkovi et al. |
| 2018/0369391 | A1 | 12/2018 | Onorato |

OTHER PUBLICATIONS

Damadorasamy, M. et al.; "Hyaluronan enhances wound repair and increases collagen III in aged dermal wounds"; Wound Repair and Regeneration, vol. 22, Issue No. 4; 2014; pp. 521-526.

Deboulle, K. et al.; "A review of the metabolism of 1,4-butanediol diglycidyl ether-crosslinked hyaluronic acid dermal fillers"; Dermatologic Surgery, vol. 39, Issue No. 12; 2013; pp. 1758-1766.

Ghazi K et al.; "Hyaluronan fragments improve wound healing on in vitro cutaneous model through P2X7 burinoreceptor basal activation: role of molecular weight"; PLoS One, vol. 7, Issue No. 11; 2012; e48351. doi: 10.1371/journal.pone.0048351.

Joddar, B. et al.; "Fragment size- and dose-specific effects of hyaluronan on matrix synthesis by vascular smooth muscle cells"; Biomaterials, vol. 27, Issue No. 15; 2006; pp. 2994-3004.

Juvederm Ultra XC; "About Juvederm Ultra XC" [product insert]; Allergan, Inc.; 2015; 4 pages.

Kablik, J. et al.; "Comparative Physical Properties of Hyaluronic Acid Dermal Fillers"; Dermatologic Surgery, vol. 35, Suppl 1; 2009; pp. 302-312.

Kaya, G. et al.; "Hyaluronate fragments reverse skin atrophy by a CD44-dependent mechanism"; PLoS Medicine, vol. 3, Issue No. 12; 2006; e493 DOI: 10.1371/journal.pmed.0030493.

Kujawa, M. et al.; "Substrate-bonded hyaluronic acid exhibits a size-dependent stimulation of chondrogenic differentiation of stage 24 limb mesenchymal cells in culture"; Developmental Biology, vol. 114, Issue No. 2; 1986; pp. 519-528.

Monheit, G. et al.; "Physical Properties of Commercial Hyaluronic Acid Dermal Fillers"; Poster presented at American Society for Dermatologic Surgery Annual Meeting; Nov. 6-9, 2008; Orlando, FL.

Monslow, J. et al.; "Hyaluronan—A Functional and Structural Sweet Spot in the Tissue Microenvironment"; Frontiers in Immunology, vol. 6, Issue 231; 2015; doi: 10.3389/fimmu.2015.00231.

Park, J. et al.; "Increase in gap junctional intercellular communication by high molecular weight hyaluronic acid associated with fibroblast growth factor 2 and keratinocyte growth factor production in normal human dermal fibroblasts"; Tissue Engineering, vol. 8, Issue No. 3; 2002; pp. 419-427.

Petrey, A. et al.; "Hyaluronan, a crucial regulator of inflammation"; Frontiers in Immunology, vol. 5, Issue No. 101; 2014; doi: 10.3389/fimmu.2014.00101.

Turner, R. et al.; "Self-Association of Hyaluronic in Aqueous NaCl Solution"; Archives of Biochemistry and Biophysics, vol. 265, Issue No. 2; 1988; pp. 484-495.

HYALURONATE COMPOSITIONS AND SOFT TISSUE FILLERS

CROSS-REFERENCE TO RELATED APPLICATIONS

This application is a divisional of U.S. application Ser. No. 16/841,861 filed on Apr. 7, 2020, which is incorporated herein by reference in its entirety.

BACKGROUND

Hyaluronic acid (HA), also known as hyaluronan or hyaluronate, is a non-sulfated glycosaminoglycan that is distributed widely throughout the human body in connective, epithelial, and neural tissues. HA is abundant in the different layers of the skin, where it has multiple functions such as to ensure good hydration, to assist in the organization of the extracellular matrix, to act as a filler material, and to participate in tissue repair mechanisms. However, with age, the quantity of HA, collagen, elastin, and other matrix polymers present in the skin decreases. For example, repeated exposed to ultraviolet light, e.g., from the sun, causes dermal cells to both decrease their production of HA as well as increase the rate of its degradation. This loss of materials results in various skin conditions such as wrinkling, hollowness, loss of moisture and other undesirable conditions that contribute to the appearance of aging.

Injectable dermal fillers have been successfully used in treating the aging skin. The fillers can replace lost endogenous matrix polymers, or enhance/facilitate the function of existing matrix polymers, in order to treat these skin conditions. Hyaluronic acid-based dermal fillers have become increasingly popular, as hyaluronic acid is a substance naturally found throughout the human body. These fillers are generally well tolerated, nonpermanent, and a fairly low risk treatment for a wide variety of skin conditions.

What is needed are HA preparations and soft tissue filler compositions containing the HA preparations wherein the properties of the HA are controlled to provide a soft tissue filler which is stable and has favorable injectability.

BRIEF SUMMARY

In one aspect, a method of making a modified hyaluronate composition, comprises
providing an aqueous solution of uncrosslinked hyaluronic acid or uncrosslinked sodium hyaluronate in unbuffered 135 mM to 200 mM NaCl, wherein the uncrosslinked hyaluronic acid or uncrosslinked sodium hyaluronate has a weight averaged molecular weight from 500-2000 kDa, and wherein the aqueous solution includes no phosphates,
crosslinking the uncrosslinked hyaluronic acid or uncrosslinked sodium hyaluronate in the aqueous solution with a dialdehyde or disulfide crosslinking agent to provide crude modified hyaluronate having a soluble fraction and a crosslinked fraction with a 10% to 98% degree of crosslinking, preferably a 10% to 60% degree of crosslinking,
centrifuging the crude modified hyaluronate and removing at least a portion of the soluble fraction, and
optionally repeating the centrifuging and removing until the modified hyaluronate has less than 10%, less than 5% or less than 2% by weight of the soluble fraction based on the total weight of hyaluronate, with a soluble fraction polydispersity (Mw/Mn) of 1 to 1.6, an Rh of the crosslinked fraction of 150 nm to 2000 nm, and an Rz of the crosslinked fraction of 50 nm to 700 nm, wherein Rh>Rz.

In another aspect, a method of making a soft tissue filler composition comprises preparing the modified hyaluronate composition as described above, and adding a collagen composition, disposing the modified hyaluronate on collagen particles, or a combination thereof.

An injectable soft tissue filler composition comprises a modified hyaluronate comprising less than 10%, less than 5% or less than 2% by weight based on the total weight of hyaluronate of a soluble fraction with a soluble fraction polydispersity (Mw/Mn) of 1 to 1.6, and a crosslinked fraction with a 10% to 98% degree of crosslinking, preferably a 10% to 60% degree of crosslinking, an Rh of 150 nm to 2000 nm, and an Rz of 50 nm to 700 nm, wherein Rh>Rz, wherein the injectable dermal filler composition comprises no phosphate buffer.

A method of filling soft tissue, comprising injecting into soft tissue of a subject in need thereof the above-described soft tissue filler composition.

The above-described and other features will be appreciated and understood by those skilled in the art from the following detailed description, drawings, and appended claims.

DETAILED DESCRIPTION

Dermal filler compositions containing HA such as Juvederm® are well-known in the art. Commercially available HA-based dermal fillers have greater than 20%, even greater than 40% of a soluble HA fraction. Because these products are under-hydrated, they can swell to greater than 300% of their volume post-injection, which causes injection site swelling and discomfort. The compositions and methods described herein avoid these problems of the prior art. By minimizing the weight percent of the soluble fraction with maximized crosslinking, post-injection swelling can be controlled.

In addition, prior art HA dermal filler compositions are typically prepared, stored and injected in phosphate buffer solution such as phosphate buffered saline (PBS). Without being held to theory, it is believed that preparation of crosslinked HA in phosphate buffer results in aggregation of HA chains, and in particular high molecular weight aggregates. As shown herein, preparation of HA in 135 mM to 200 mM NaCl provides a reduction in self-association of HA segments which is expected to provide a higher quality dermal filler than the prior art compositions prepared in phosphate buffer.

In addition, removal of low molecular weight HA fractions (<50, <100 and <250 kDa), which are prevalent in the soluble HA fraction, will alleviate FDA concerns that low molecular weight HA may be inflammatory and/or pro-fibrotic.

In order to provide an improved modified HA preparation, the inventor has studied the relationship of fluid (soluble or non-modified hyaluronate) and gel (modified or crosslinked hyaluronate). The use of combined Dynamic Light Scattering (DLS) with Multi-angle (three or greater) laser light scattering (MALS) in-line with a refractive index detector (RI) provides excellent analytical tools for comparing Radius of Hydration (Rh) with Root Mean Square Radius (Rz).

The relationship of Rh to Rz provides conformation information on the HA compositions. An Rh greater than Rz suggests a spherical structure of the HA. The composition that results in an Rz greater than Rh suggests an elongated, branched, or linear HA structure. Measuring the Rz and Rh allows one to manufacture a modified HA composition in a controlled manner to favor the spherical structure. For example:

Rh>Rz=Globular and Spherical (Purified/retained modified hyaluronate network of polymer)

Rh<Rz=Elongation and linear (Reduced non-modified hyaluronate)

Figure 1:
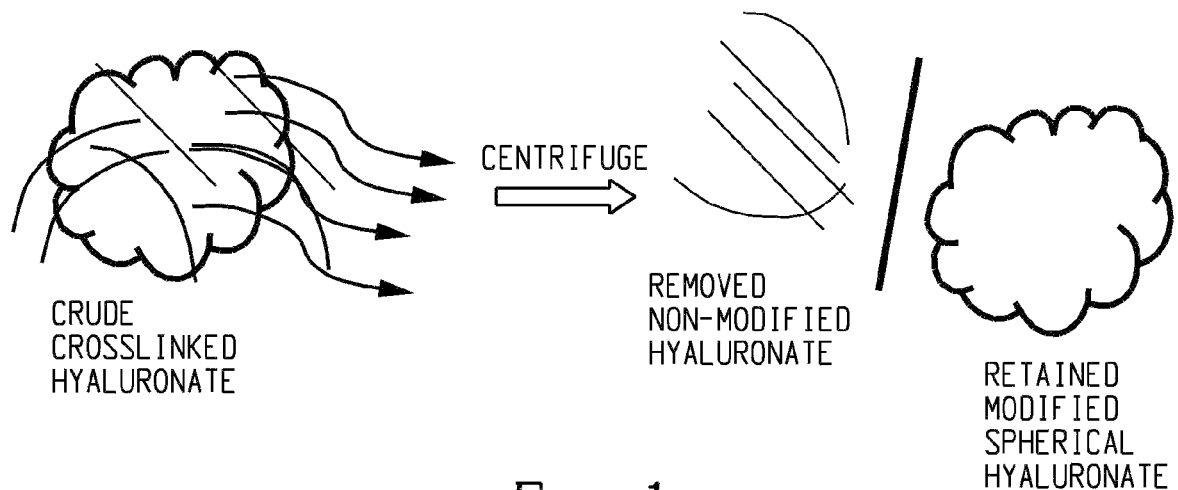
FIG. 1 is a schematic of the purification of crude crosslinked hyaluronate to provide removed non-modified hyaluronate and retained modified spherical hyaluronate according to an aspect of the present disclosure.

FIG. 1 is a schematic illustrating the purification of crude crosslinked hyaluronate to provide removed non-modified (linear and elongated) hyaluronate and retained modified spherical hyaluronate according to an aspect of the present disclosure. The use of combined Dynamic Light Scattering (DLS) with Multi-angle (three or greater) laser light scattering (MALS) in-line with a refractive index detector (RI) has allowed the inventor to identify modified HA preparations with improved properties as soft tissue/dermal fillers.

Modified hyaluronate, as used herein, refers to hyaluronate having a high degree of crosslinking (e.g., greater than 10% crosslinking, defined as the percent weight ratio of the crosslinking agent to HA-monomeric units within the crosslinked portion of the HA) in a crosslinked portion and a low weight percentage of soluble, that is uncrosslinked, hyaluronate (e.g., <10% by weight of the HA is uncrosslinked, soluble HA).

In an aspect, a method of making a modified hyaluronate composition comprises providing an aqueous solution of uncrosslinked hyaluronic acid or uncrosslinked sodium hyaluronate in unbuffered 135 mM to 200 mM NaCl, wherein the uncrosslinked hyaluronic acid or uncrosslinked sodium hyaluronate has a weight averaged molecular weight from 500-2000 kDa, and wherein the aqueous solution includes no phosphates. The uncrosslinked hyaluronic acid or uncrosslinked sodium hyaluronate in the aqueous solution is then crosslinked with a dialdehyde or disulfide crosslinking agent to provide crude modified hyaluronate having a soluble fraction and a crosslinked fraction with a 10% to 98% degree of crosslinking, preferably a 10% to 60% degree of crosslinking. The crude modified hyaluronate is then centrifuged to remove at least a portion of the soluble fraction. The centrifuging and removing is repeated until the modified hyaluronate has less than 10%, less than 5%, or less than 2% by weight of the soluble fraction based on the total weight of hyaluronate. The modified hyaluronate further has a soluble fraction polydispersity (Mw/Mn) of 1 to 1.6, an Rh of the crosslinked fraction of 150 nm to 2000 nm, and an Rz of the crosslinked fraction of 50 nm to 700 nm, wherein Rh>Rz.

As used herein, the term "crosslinked" refers to the intermolecular bonds joining the individual polymer molecules, or monomer chains, into a more stable structure like a gel. As such, a crosslinked HA has at least one intermolecular bond joining at least one individual polymer molecule to another one. The crosslinking of HA typically result in the formation of a hydrogel.

Degree of crosslinking as used herein refers to the intermolecular junctions joining the individual HA polymer molecules, or monomer chains, into a permanent structure, or as disclosed herein the soft tissue filler composition. Moreover, degree of crosslinking for purposes of the present disclosure is further defined as the percent weight ratio of the crosslinking agent to HA-monomeric units within the crosslinked portion of the HA based composition. It is measured by the weight ratio of crosslinker to HA monomers (crosslinker:HA monomers).

Soluble HA, sometimes referred to as free HA, refers to individual HA polymer molecules that are not crosslinked, or very lightly crosslinked (very low degree of crosslinking). The highly crosslinked (higher degree of crosslinking) macromolecular structure makes up most of the soft tissue filler composition. Soluble HA generally remains water soluble. Soluble HA can alternatively be defined as the "uncrosslinked," or lightly crosslinked component of the macromolecular structure making up the soft tissue filler composition disclosed herein.

Based on the prior art such as U.S. Pat. No. 10,391,202, it is believed that a high percentage of soluble HA is required to provide sufficient injectability for use as a soft tissue filler. Specifically, the prior art HA gels can be considered as crosslinked HA in a relatively fluidic medium of free HA. The inventor of the present application has found that HA with an Rh greater than Rz, that is, HA with a spherical structure as illustrated in FIG. 1, provides improved injectability by reducing swelling of the gel composition. Thus, a high amount of soluble HA is not required to provide injectability. In an aspect, the Rh:Rz of the crosslinked fraction is 3 to 1, favoring a substantially spherical structure.

The underhydrated HA with Rh greater than Rz and a low amount of soluble fraction provides a reduction in excess fluid that, in addition to providing an injectable composition, also decreases epoxide degradation which is seen in prior art compositions. Thus, when the crosslinking agent comprises a dialdehyde crosslinking agent, the modified HA exhibits reduced hydraulic swelling measured as water uptake, no visible phase separation or viscosity reduction, less than 30% hydrolysis of ether linkages upon storage at 4 to 37° C. for 730 days, or a combination thereof.

Another advantage of the compositions disclosed herein is the small particle size of the modified HA. In prior art compositions, the crosslinked HA particles would have diameters of greater than 200 μm. In aspects, the modified HA described herein is nanosized having an average particle size of less than about 2 μm (2000 nm). The modified hyaluronate further has a soluble fraction polydispersity (Mw/Mn) of 1 to 1.6, an Rh of the crosslinked fraction of 150 nm to 2000 nm, and an Rz of the crosslinked fraction of 50 nm to 700 nm, wherein Rh>Rz.

In an aspect, the soluble fraction comprises less than 1%, 2% or 4% by weight of hyaluronate having a molecular weight less than 250 kDa based on the weight of the hyaluronate.

In an aspect, the crosslinking is performed at a temperature greater than 20° C., preferably 25-40° C.

Exemplary crosslinking agents include pentaerythritol tetraglycidyl ether (PETGE), divinyl sulfone (DVS), 1,4-butanediol diglycidyl ether (BDDE), 1,4-bis(2,3-epoxypropoxy)butane, 1,4-bisglycidyloxybutane, 1,2-bis(2,3-epoxy propoxy)ethylene and 1-(2,3-epoxypropyl)-2,3- epoxycyclohexane, 1,2-bis(2,3-epoxypropoxy)ethylene (EGDGE), 1,2,7,8-diepoxyoctane (DEO), (phenylenebis-(ethyl)-carbodiimide and 1,6 hexamethylenebis (ethylcarbodiimide), adipic dihydrazide (ADH), bis(sulfosuccinimidyl) suberate (BS), hexamethylenediamine (NMDA), 1-(2,3-epoxypropyl)-2,3-epoxycyclohexane, lysine, lysine methylester, or a combination thereof.

In an aspect, after centrifuging and removing, the modified hyaluronate can be washed with a solution having a pH of 4.5 to 5.5. This optional washing step can increase the flow of the fluid comprising the modified hyaluronate as a single resultant mass even after the pH is subsequently increased to 5.5 to 7 and even up to pH 8. Without being held to theory, it is believed that washing provides for different structural properties to be obtained, such as formation of a co-joined mass of volumetric size, that is, an aggregate of nanostructured particles providing a larger overall mass. Thus, while the modified hyaluronate remains nanostructured, it can be conveniently grouped as a large homogenous mass.

In an aspect, the method further comprises adding 200 to 590 ppm of a local anesthetic, e.g., lidocaine, to the aqueous solution of uncrosslinked hyaluronic acid or uncrosslinked sodium hyaluronate prior to crosslinking. As described in U.S. Pat. No. 10,391,202, lidocaine is added to an HA composition after crosslinking of the HA. This addition of lidocaine after crosslinking results in a lack of control of the lidocaine in the solution. Lidocaine addition to the non-crosslinked fraction advantageous because: 1) lidocaine is a separate entity that is best served in a least manipulated state during processing, thus inclusion with non-crosslinked hyaluronate and then crosslinking provides a composition with defined components; and 2) addition to the non-modified HA component makes it easier to determine that the soluble fraction is taken advantage of for its limited residence time post-injection, and it is best suited to accommodate and facilitate the solubilization of the lidocaine, specifically lidocaine monohydrate hydrochloride.

Exemplary local anesthetics include ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, and salts thereof. In an aspect, the local anesthetic agent is lidocaine, such as in the form of lidocaine HCl. The concentration of lidocaine in the compositions described herein can be therapeutically effective meaning the concentration is adequate to provide a therapeutic benefit without inflicting harm to the patient.

In an aspect, the lidocaine is added as lidocaine hydrochloride monohydrate, CAS 6108-05-0, average molecular weight 288.81 g/mol, and not anhydrous lidocaine hydrochloride, CAS 73-78-9, average molecular weight 270.8 g/ml. Advantageously, adding the lidocaine hydrochloride in the form of the monohydrate and not anhydrous is predicted to improve the solubility of the lidocaine in the HA and eliminate the dose-dumping observed with prior art compositions. The use of lidocaine hydrochloride monohydrate provides a solubilized lidocaine that does not freely release in solution, rather remaining associated with the HA.

Also included herein the product of the processes to make modified HA as described herein.

While the modified HA described herein can be used as a soft tissue/dermal filler composition, soft tissue/dermal filler compositions can also include collagen. In an aspect, a collagen composition can be added to the modified HA, the modified HA can be disposed on collagen particles, or a combination thereof. The collagen can be in the form of collagen hollow spheres, collagen microparticles, collagen fibers, or a combination thereof. Collagen particles can have average diameters of 20 um to 250 um.

In an aspect, the collagen comprises collagen fibers and the collagen fibers are comingled with the modified hyaluronate. Comingling can be done by mixing collage fibers with crosslinked HA and entangling, such as by freeze-drying, or by use of crosslinking using the crosslinking agents described above.

In an aspect, an injectable soft tissue filler composition, comprises a modified hyaluronate comprising less than 10%, less than 5% or less than 2% by weight based on the total weight of hyaluronate of a soluble fraction with a soluble fraction polydispersity (Mw/Mn) of 1 to 1.6, and a crosslinked fraction with a 10% to 98% degree of crosslinking, preferably a 10% to 60% degree of crosslinking, an Rh of 150 nm to 2000 nm, and an Rz of 50 nm to 700 nm, wherein Rh>Rz, wherein the injectable dermal filler composition comprises no phosphate buffer. In an aspect, the injectable soft tissue filler composition comprises 35 to 200 nM NaCl, preferably 150 mM NaCl as a non-buffering suspending solution. The injectable soft tissue filler can be in the form of a reconstituted lyophilized foam, or an aqueous gel-like material.

When the injectable soft tissue filler is in the form of a reconstituted lyophilized foam, the foam form can be freeze dried without topical anesthetic. The foam can them be rehydrated with NaCl and topical anesthetic for administration. Storage as a foam advantageously reduced the potential for hydrolytic degradation of crosslinked HA and provides a storage option for bulk production.

In an aspect, the modified HA has an average particle size of less than about 2 μm (2000 nm).

The injectable soft tissue filler composition can include 200 to 590 ppm topical anesthetic, e.g., lidocaine. Because the lidocaine is added during the crosslinking step, the lidocaine can be solubilized in the HA, preventing dos dumping of free lidocaine.

In an aspect, the viscosity of the soft tissue filler composition is about 50 Pa*s to about 450 Pa*s. In other embodiments, the viscosity can be from about 50 Pa*s to about 300 Pa*s, from about 100 Pa*s to about 400 Pa*s, or about 250 Pa*s to about 400 Pa*s, or about 50 Pa*s to about 250 Pa*s.

Generally, the concentration of HA in soft tissue filler composition is preferably at least 10 mg/mL and up to about 40 mg/mL, specifically 15 mg/ml to 30 mg/ml. For example, the concentration of HA in some of the compositions is in a range between about 20 mg/mL and about 30 mg/mL. Further, for example, in some embodiments, the compositions have a HA concentration of about 22 mg/mL, about 24 mg/mL, about 26 mg/mL, or about 28 mg/mL. Concentrations of 5 to 10 mg/ml can be used for sensitive injection areas such as thin skin and less dynamic movement regions.

The soft tissue filler compositions can be introduced into syringes and optionally sterilized. Syringes are those capable of delivering viscous dermal filler compositions. The syringes generally have an internal volume of about 0.4 mL to about 3 mL, more preferably between about 0.5 mL and about 1.5 mL or between about 0.8 mL and about 2.5 mL. This internal volume is associated with an internal diameter of the syringe which plays a key role in the extrusion force needed to inject high viscosity dermal filler compositions. The internal diameters are generally about 4 mm to about 9 mm, more preferably from about 4.5 mm to about 6.5 mm or from about 4.5 mm to about 8.8 mm. Further, the extrusion force needed to deliver the HA/lidocaine compositions from the syringe is dependent on the needle gauge. The gauges of needles used generally include gauges between about 18 G and about 40 G, more preferably about 27 G to about 31 G or from about 25 G to about 27 G. A person of ordinary skill in the art can determine the correct syringe dimensions and needle gauge required to arrive at a particular extrusion force requirement. For example, 27 to 31 G needles are desirable for minimal injection site trauma, while deeper and high dosage delivery can utilize 25 to 27 G needles.

The extrusion forces displayed by the soft tissue filler compositions described herein using the needle dimensions described above are at an injection speeds that are comfortable to a patient. Comfortable to a patient is used to define a rate of injection that does not injure or cause excess pain to a patient upon injection to the soft tissue. One skilled in the art will appreciate that comfortable as used herein includes not only patient comfort, but also comfort and ability of the physician or medical technician injecting the soft tissue filler compositions. Although certain extrusion forces may be achievable with the soft tissue filler compositions of the present disclosure, one skilled in the art understands that high extrusion forces can lead to lack of control during injection and that such lack of control may result in additional pain to the patient. Extrusion forces of the present soft tissue filler compositions should not exceed 20 N, such as about 8 N to about 15 N, or more preferably from about 10 N to about 13 N, or about 11 N to about 12 N, for example, at an extrusion rate of about 12.5 mm/min. For example, an exemplary extrusion force is not to exceed 20N continuous nor peak force (newtons) from 25.4 mm through 50 or more mm per min extrusions with 27 G or 30 G needles.

Sterilization, as used herein comprises any method known in the art to effectively kill or eliminate transmissible agents, preferably without substantially altering of degrading the soft tissue filler compositions. A lyophilized form can be effectively sterilized with dry heat autoclaving, and similar sterilization assurance can be gained by steam or dry autoclaving for syringe enclosure gel compositions. In specific applications, such as fine lines and large dose delivery, pulsed light methods of xenon or LED can be utilized.

A method of filling soft tissue comprises injecting into soft tissue of a subject in need thereof modified HA or a soft tissue filler composition as described herein. In an aspect, the injected composition comprises no phosphate buffer. In another aspect, wherein the injected composition comprises 135 mM to 200 mM NaCl.

Exemplary soft tissues include comprises laugh lines, smile lines, crow's feet, wrinkles, and facial creases.

Use of the modified hyaluronate as described herein is expected to improve predictable implant performance, provide repeatable metrics for injection force, and reduce unwanted biological responses once implanted.

The invention is further illustrated by the following non-limiting examples.

EXAMPLES

Methods

Example 1: Analysis of As-Received HA

Figure 2:
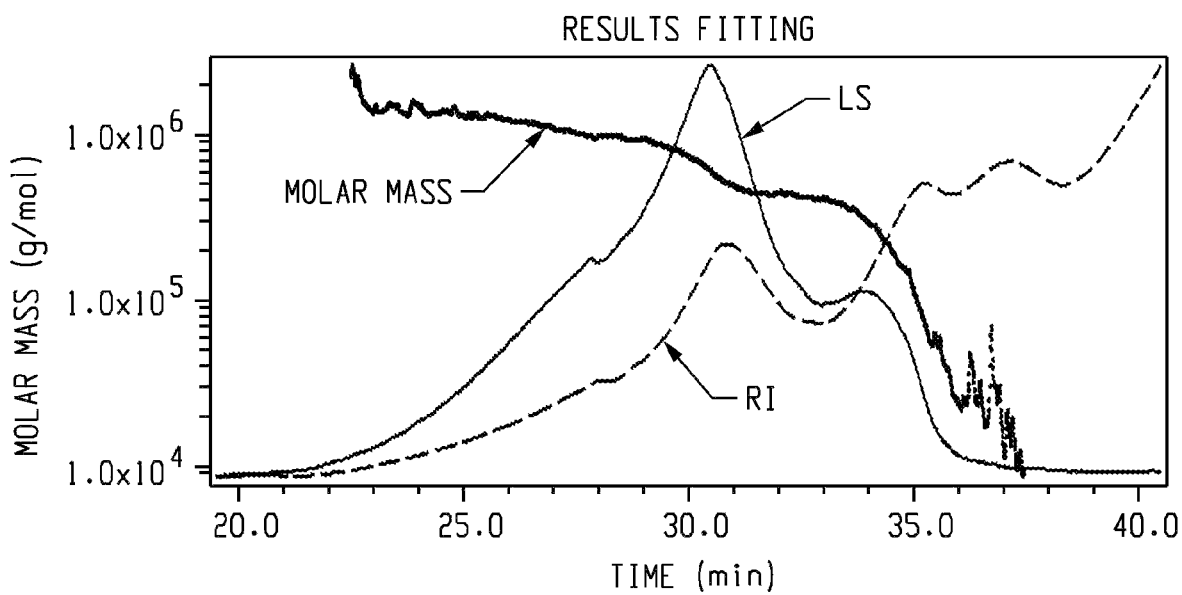
FIG. 2 shows fitted light scattering results for as-received HA.

A SEC MALS RI analysis was performed on as-received HA. The as-received HA includes various manufactured HA composites that had been crosslinked. These composites still contain significant soluble fractions of hyaluronate, even after processing with crosslinker has been completed. The soluble fractions are then removed. The flow rate was 0.500 mL/min, the calibration constant of the DAWN light scattering instrument was $5.7653 \times 10^{-5}$ 1/(V/cm), the RI instrument was from Optilab, the solvent was aqueous PBS with a refractive index of 1.331. The light scattering model was Berry with a fit degree of 2 and a do/dc (mL/g) of 1.650. The fitted results are shown in FIG. 2 and Tables 1 and 2 include the numerical data.

TABLE 1

Peak 1 Results for As-Received HA

| Parameter | As-received HA |
|---|---|
| Calculated mass (μg) | 396.14 |
| Mass fraction (%) | 100 |
| Mw, Da | $4.221 \times 10^5$ |
| Mw/Mn | 6.217 |
| Rz, nm | 107.9 |

TABLE 2

Distribution Analysis for As-Received HA

| Range | Molar Mass | Cumulative % |
|---|---|---|
| 1 | 0-50,000 Da | 24.4 |
| 2 | 0-100,000 Da | 32.2 |
| 3 | 0-250,000 Da | 41.8 |
| 4 | 100,000-200,000 Da | 9.2 |
| 5 | 0-300,000 Da | 100 |

This example illustrates that:

The as-received HA includes a large percentage of low molecular weight HA which the FDA has determined to be undesirable.

The as-received HA is labeled as 150 kDa by the manufacturer, but does not specify polydispersity. Per the analysis, the Mw is 422 kDa and the polydispersity of the as-received HA is high at 6.2. Thus, the molecular weight is higher than reported and the polydispersity is extremely high.

Only 9.2% of the as-received HA is in the target molecular weight range of 100-200 kDa.

Example 2: SEC MALS RI Analysis of Crosslinked, Purified HA

A SEC MALS RI analysis was performed on as-received HA after crosslinking and after two rounds of purification by centrifugation. Instrument parameters were the same as in Example 1. The fitted results are shown in Tables 3 and 4.

TABLE 3

Peak results for Crosslinked HA, And After Two Rounds of Centrifugation

| Parameter | As-received Crosslinked HA | After first pass purification | After second pass purification |
|---|---|---|---|
| Mn, Da | $6.789 \times 10^4$ | $1.74 \times 10^5$ | $4.453 \times 10^5$ |
| Mw, Da | $4.221 \times 10^5$ | $1.338 \times 10^6$ | $2.371 \times 10^6$ |
| Mw/Mn | 6.217 | 7.691 | 5.325 |
| Rz, nm | 107.9 | 103.7 | 110.5 |
| Rh (avg, nm) | 36.9 | 36.92 | 36.9 |

TABLE 4

Distribution results for Crosslinked HA, And After Two Rounds of Centrifugation

| Range | Molar Mass | Cumulative % As received HA | Cumulative % After First Pass Purification | Cumulative % After Second Pass Purification |
|---|---|---|---|---|
| 1 | 0-50,000 Da | 24.4 | 6.65 | 0 |
| 2 | 0-100,000 Da | 32.2 | 24.0 | 3.575 |
| 3 | 0-250,000 Da | 41.8 | 40.7 | 19.323 |
| 4 | 100,000-200,000 Da | 9.3 | 31.779 | 32.428 |

This example clearly shows a reduction in the 0-50 and 1-100 kDA fractions and enrichment of the 100-200 kDa fraction after two rounds of centrifugation.

Example 3: SEC MALS RI Analysis of Crosslinked HA

As-received Sodium HA 1.5M Da was hydrated in distilled water. The solution was adjusted to 150 mM NaCl. The HA was crosslinked with BDDE in the 150 mM NaCl solution at 23 to 37° C. for 20 to 60 min. After crosslinking, the sample was centrifuged at 10 G for 15 minutes. Instrument parameters were the same as in Example 1.

TABLE 5

Peak results for Crosslinked, Purified HA

| Parameter | As-received Crosslinked HA |
|---|---|
| Calculated mass (μg) | 17.54 |
| Rz, nm | 132 |
| Rh (avg, nm) | 236 |

TABLE 6

Distribution results for Crosslinked, Purified HA

| Range | Molar Mass | Cumulative % As received HA |
|---|---|---|
| 1 | 0-50,000 Da | 0 |
| 2 | 0-100,000 Da | 0 |
| 3 | 0-250,000 Da | 0 |
| 4 | 250,000-1,000,000 Da | 68.3 |
| 5 | 100,000-200,000 Da | 25.6 |
| 6 | 200,000-3,122,965 | 6.1 |

Importantly, the fractions <50 k, <100 k, and <250 kDa fractions are all essentially zero. An Rh>Rz (236 vs 132 nm) shows that globular structures dominate the material. A tight distribution of nanometer globular structures (approx. 230 nm) with Rh>Rz was achieved.

Example 4: Comparison of NaCl and Phosphate Buffer, As Received HA

4 MDa raw material sodium hyaluronate powder was put into solution with PBS (no calcium, no magnesium to provide no disruption to the conformation of HA) to provide a 20 mg/ml concentration. The 20 mg/ml solution was used to provide 2 aliquots.

Aliquot 1: diluted 1:10 with PBS (no calcium, no magnesium)

Aliquot 2: diluted 1:10 with 150 mM NaCl (no calcium, no magnesium)

The samples were vortexed and 500 μl of a 0.2 mg/ml solution was injected. Instrument conditions were as in Example 1.

TABLE 7

Peak results for NaCl compared to phosphate buffer, as-received HA

| | Phosphate | NaCl |
|---|---|---|
| Mn | $1.562 \times 10^6$ | $1.682 \times 10^6$ |
| Mw | $1.887 \times 10^6$ | $1.822 \times 10^6$ |
| Mw/Mn | 1.208 | 1.083 |
| Rh (Q)z | 69.41 | 49.88 |
| Rz | 175.8 | 168.6 |

TABLE 8

Distribution results for NaCl compared to phosphate buffer, as-received HA

| | Phosphate | NaCl |
|---|---|---|
| 0-50 kDa | 0 | 0 |
| 0-100 kDa | 0 | 0 |
| 0-250 kDa | 0 | 0 |
| 250-2,000 kDa | 30.6 | 65.499 |
| 2,000-3,000 kDa | 68.2 | 34.53 |
| 0-4,000 kDa | 99.5 | 99.987 |

When the raw material was dissolved in NaCl vs phosphate buffer, there was a significant difference in Rh values, with Rz and Mw being similar.

Example 5: Comparison of NaCl and Phosphate Buffer, Crosslinked HA

A large sample of HA (7 liters) was prepared and diluted with either PBS or NaCl. The samples were then crosslinked, and centrifuged to remove the soluble fraction. The results are provides in Tables 7 and 8.

TABLE 9

Peak results for NaCl compared to phosphate buffer, crosslinked HA

| | PBS | NaCl |
|---|---|---|
| Hydrodynamic radius Rh (nm) | 44.65 | 41.46 |
| Rz (nm) | 105.4 | 103.8 |
| Polydispersity Mw/Mn | 6.59 | 1.503 |
| Mn | $4.832 \times 10^4$ | $3.605 \times 10^5$ |
| Mw | $3.187 \times 10^5$ | $5.418 \times 10^5$ |

TABLE 10

Distribution results for NaCl compared to phosphate buffer, crosslinked HA

|  | PBS | NaCl |
|---|---|---|
| 0-50,000 g/mol | 35.5 | 0 |
| 0-100,000 g/mol | 40.3 | 0 |
| 0-250,000 g/mol | 54.49 | 19.4 |
| 250,000-2,000,000 g/mol | 45.4 | 80.535 |
| 0-3,000,000 g/mol | 99.97 | 99.98 |

The analysis is the finished/final product residual soluble fractions.

Identical Peak Limits (min) 11.350-22.000

35% reduction in 0 to 50 k Da soluble fraction in NaCl processing

40% reduction in 0 to 100 k Da soluble fraction in NaCl processing

35% reduction in 0 to 250 k Da soluble fraction in NaCl processing

Reduced polydispersity in NaCl process—1.5 vs 6.5 (Mw/Mn)

Example 6: Use of HPLC/SEC/MALS/RI to Verify Reduction of the Soluble HA Component Starting material HA was crosslinked with homobifunctional 1,4-butanediol diglycidyl ether (BDDE). Two centrifugation steps were performed under conditions 10 to 12 G for 15 minutes.

The analytical method of HPLC/SEC/MALS/RI (High Pressure Liquid Chromatography-Size Exclusion Chromatography with Multi-Angle Light Scattering-Refractive Index Detection) was validated for determining the number average molecular weight, weight average molecular weight, Rz and wt % soluble HA. Mobile Phase was 150 mM NaCl or 150 mM NaNO$_3$, flowrates of 0.3 to 0.8 ml/min, with Shodex™ LB 805 and 804 columns run in tandem, or dual Shodex™ LB 806M (mixed bed columns—run in tandem).

Figure 3:
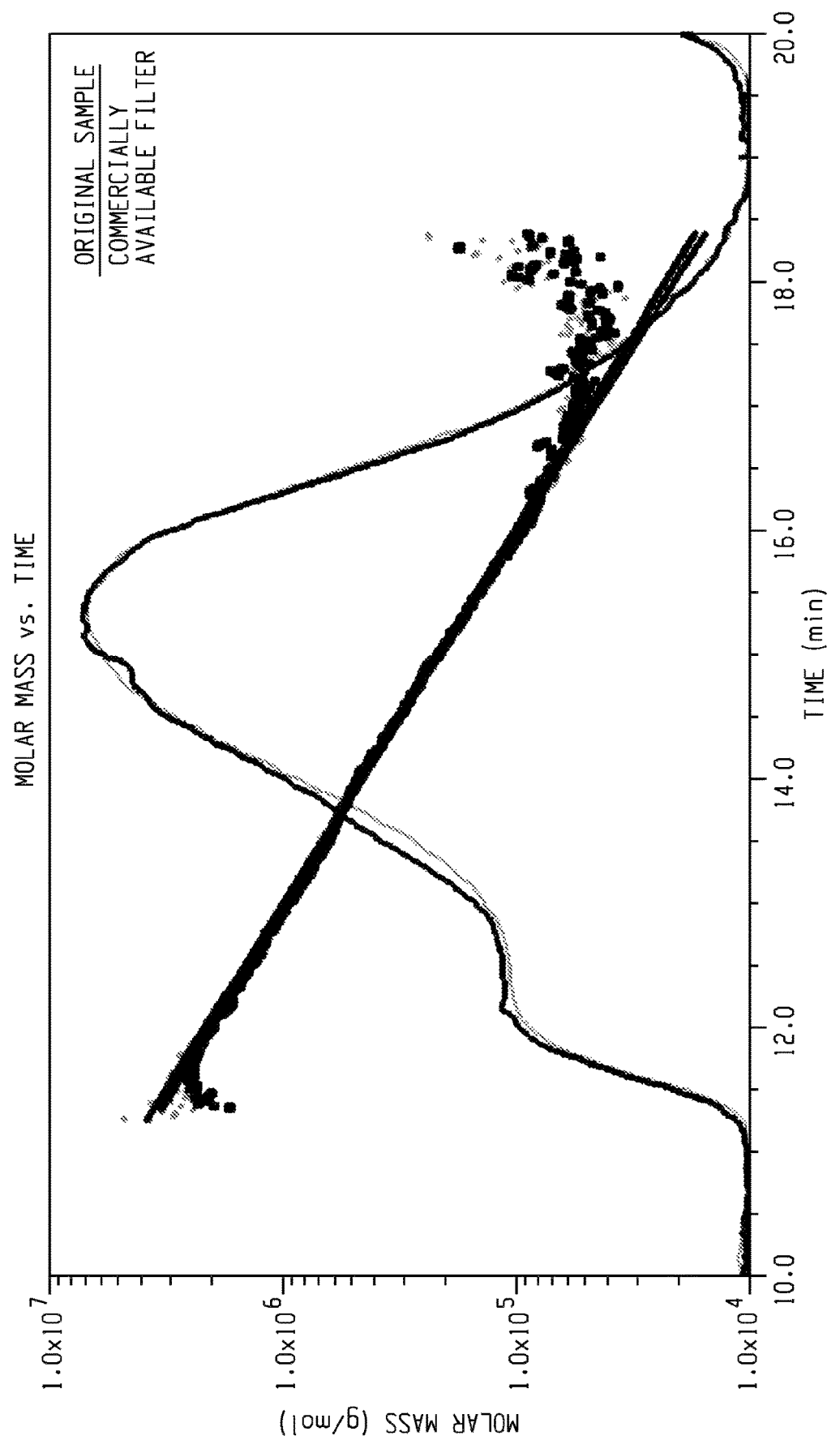
FIGS. 3-5 show the original crosslinked material, first purification and second purification, respectively, as soluble HA is removed from the crosslinked HA to provide modified HA.
Figure 4:
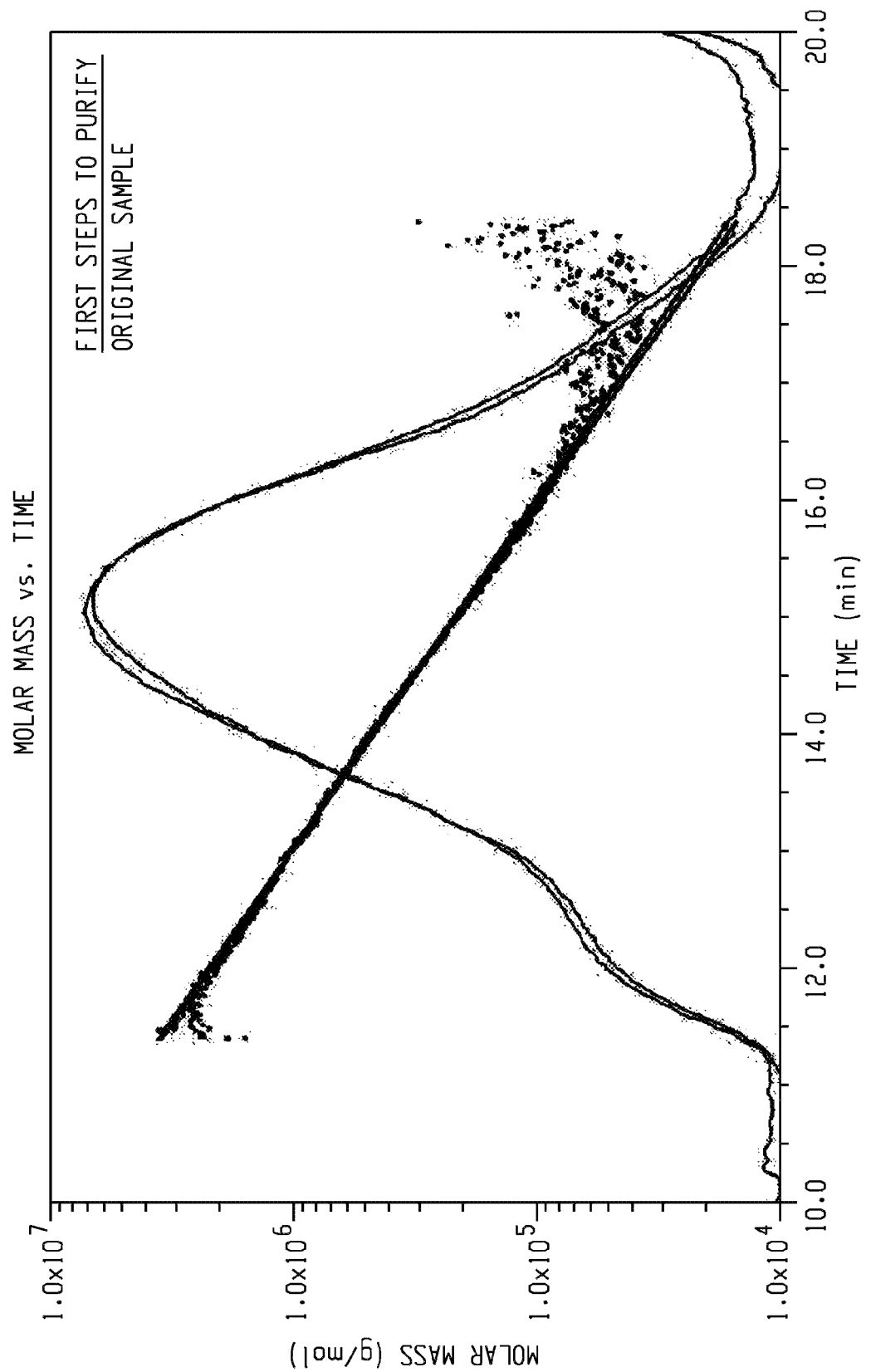
Figure 5:
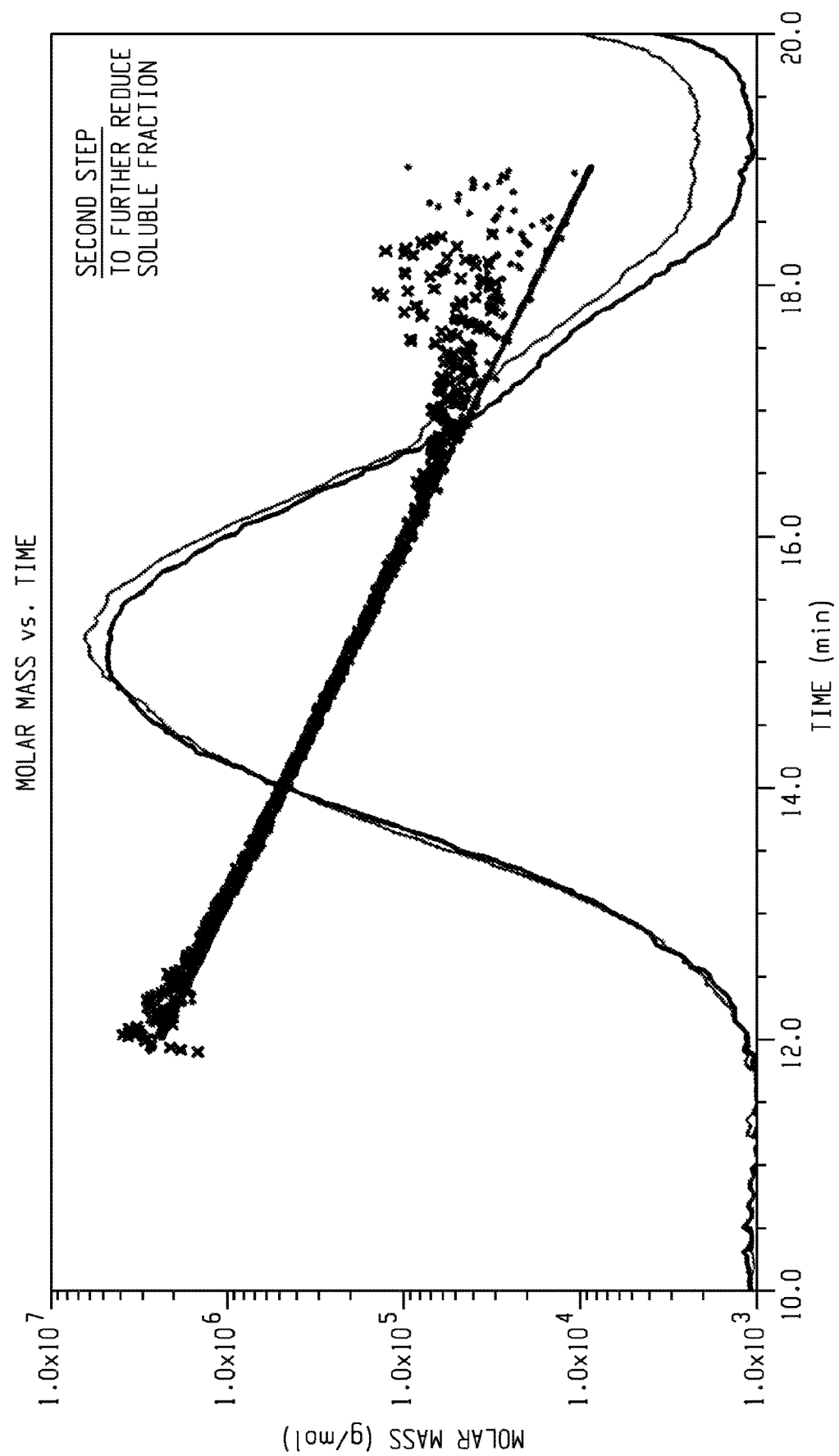

Table 9 and FIGS. 3-5 show the original crosslinked material, first centrifugation and second successive centrifugation, respectively.

TABLE 11

Parameters for reduction of soluble HA

| Parameter | Original sample | First centrifugation | Second centrifugation |
|---|---|---|---|
| Mn, kDa | 140 | 130 | 130 |
| Mw, kDa | 460 | 430 | 420 |
| Mw/Mn | 3.3 | 3.3 | 3.2 |
| Rz, nm | 135 | 123 | 115 |
| wt % soluble HA | 21% | 15% | 10% |

The amount of soluble HA was reduced by more than 50% using two centrifugation steps. The material with 10 wt % soluble HA has a much lower wt % HA than commercially available HA-based dermal fillers, which have more than 20 wt % and even more than 40 wt % soluble HA.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of making a modified hyaluronate composition, comprising providing an aqueous solution of uncrosslinked hyaluronic acid or uncrosslinked sodium hyaluronate in unbuffered 135 mM to 200 mM NaCl, wherein the uncrosslinked hyaluronic acid or uncrosslinked sodium hyaluronate has a weight averaged molecular weight from 500-2000 kDa, and wherein the aqueous solution includes no phosphates, crosslinking the uncrosslinked hyaluronic acid or uncrosslinked sodium hyaluronate in the aqueous solution with a dialdehyde or disulfide crosslinking agent to provide crude modified hyaluronate having a soluble fraction and a crosslinked fraction with a 10% to 98% degree of crosslinking, wherein the soluble fraction comprises less than 4% by weight of hyaluronate having a molecular weight less than 250 kDa based on the weight of the hyaluronate, centrifuging the crude modified hyaluronate and removing at least a portion of the soluble fraction, and optionally repeating the centrifuging and removing until the modified hyaluronate has less than 10% by weight of the soluble fraction based on the total weight of hyaluronate, with a soluble fraction polydispersity (Mw/Mn) of 1 to 1.6, an Rh of the crosslinked fraction of 150 nm to 2000 nm, and an Rz of the crosslinked fraction of 50 nm to 700 nm, wherein Rh>Rz.

2. The method of claim 1, wherein the ratio of Rh:Rz of the crosslinked fraction is 3 to 1.

3. The method of claim 1, wherein the modified HA has an average particle size of less than about 2 µm (2000 nm).

4. The method of claim 1, further comprising adding 200 to 590 ppm of a local anesthetic to the aqueous solution of uncrosslinked hyaluronic acid or uncrosslinked sodium hyaluronate prior to crosslinking.

5. The method of claim 4, wherein the topical anesthetic is lidocaine hydrochloride monohydrate.

6. The method of claim 1, wherein the crosslinking agent comprises a dialdehyde crosslinking agent and the modified HA exhibits reduced hydraulic swelling measured as water uptake, no visible phase separation or viscosity reduction, less than 30% hydrolysis of ether linkages upon storage at 4 to 37° C. for 730 days, or a combination thereof.

7. The method of claim 1, wherein the crosslinking is performed at a temperature greater than 20° C.

8. The method of claim 1, wherein the dialdehyde or disulfide crosslinking agent comprises pentaerythritol tetraglycidyl ether (PETGE), divinyl sulfone (DVS), 1,4-butanediol diglycidyl ether (BDDE), 1,4-bis(2,3-epoxypropoxy)butane, 1,4-bisglycidyloxybutane, 1,2-bis(2,3-epoxypropoxy)ethylene and 1-(2,3-epoxypropyl)-2,3-epoxycyclohexane, 1,2-bis(2,3-epoxypropoxy)ethylene (EGDGE), 1,2,7,8-diepoxyoctane (DEO), (phenylenebis-(ethyl)-carbodiimide and 1,6 hexamethylenebis (ethylcarbodiimide), adipic dihydrazide (ADH), bis(sulfosuccinimidyl) suberate (BS), hexamethylenediamine (NMDA), 1-(2,3-epoxypropyl)-2,3-epoxycyclohexane, lysine, lysine methylester, or a combination thereof.

9. The method of claim 1, further comprising after centrifuging and removing, washing the modified hyaluronate with a solution having a pH of 4.5 to 5.5.

10. A method of making a soft tissue filler composition, comprising preparing the modified hyaluronate composition according to the method of claim 1 and adding a collagen composition, disposing the modified hyaluronate on collagen particles, or a combination thereof.

11. The method of claim 10, wherein the collagen composition comprises collagen hollow spheres, collagen microparticles, collagen fibers, or a combination thereof.

12. The method of claim 11, wherein the collagen composition comprises collagen fibers and the collagen fibers are comingled with the modified hyaluronate.

13. A method of making a modified hyaluronate composition, comprising
providing an aqueous solution of uncrosslinked hyaluronic acid or uncrosslinked sodium hyaluronate and 200 to 590 ppm lidocaine hydrochloride monohydrate in unbuffered 135 mM to 200 mM NaCl, wherein the uncrosslinked hyaluronic acid or uncrosslinked sodium hyaluronate has a weight averaged molecular weight from 500-2000 kDa, and wherein the aqueous solution includes no phosphates,
crosslinking the uncrosslinked hyaluronic acid or uncrosslinked sodium hyaluronate in the aqueous solution with a dialdehyde or disulfide crosslinking agent to provide crude modified hyaluronate having a soluble fraction and a crosslinked fraction with a 10% to 98% degree of crosslinking,
centrifuging the crude modified hyaluronate and removing at least a portion of the soluble fraction, wherein the soluble fraction comprises less than 4% by weight of hyaluronate having a molecular weight less than 250 kDa based on the weight of the hyaluronate, and
optionally repeating the centrifuging and removing until the modified hyaluronate has less than 10% by weight of the soluble fraction based on the total weight of hyaluronate, with a soluble fraction polydispersity (Mw/Mn) of 1 to 1.6, an Rh of the crosslinked fraction of 150 nm to 2000 nm, and an Rz of the crosslinked fraction of 50 nm to 700 nm, wherein Rh>Rz.

\* \* \* \* \*